United States Patent
Trinkaus (10) Patent No.: US 12,304,187 B2
(45) Date of Patent: May 20, 2025

(54) METHOD FOR PRODUCING AN ELASTIC LAMINATE, AND LAMINATE OBTAINABLE ACCORDING TO SAID METHOD

(71) Applicant: Nitto Advanced Film Gronau GmbH, Gronau (DE)

(72) Inventor: Jan Michael Trinkaus, Euskirchen (DE)

(73) Assignee: Nitto Advanced Film Gronau GmbH, Gronau (DE)

( * ) Notice: Subject to any disclaimer, the term of this patent is extended or adjusted under 35 U.S.C. 154(b) by 0 days.

(21) Appl. No.: 17/774,714

(22) PCT Filed: Nov. 6, 2019

(86) PCT No.: PCT/EP2019/080423
§ 371 (c)(1),
(2) Date: May 5, 2022

(87) PCT Pub. No.: WO2021/089141
PCT Pub. Date: May 14, 2021

(65) Prior Publication Data
US 2022/0396063 A1    Dec. 15, 2022

(51) Int. Cl.
*B32B 37/02*    (2006.01)
*B32B 3/28*    (2006.01)
(Continued)

(52) U.S. Cl.
CPC ............. *B32B 37/02* (2013.01); *B32B 3/28* (2013.01); *B32B 5/022* (2013.01); *B32B 5/06* (2013.01);
(Continued)

(58) Field of Classification Search
CPC .. B32B 37/02; B32B 7/05; B32B 3/28; B32B 5/022; B32B 5/06; B32B 7/08;
(Continued)

(56) References Cited

U.S. PATENT DOCUMENTS 5,167,897 A    12/1992    Weber et al.
5,681,302 A  *  10/1997    Melbye ............. A61F 13/15593
                                                        604/385.22
(Continued)

FOREIGN PATENT DOCUMENTS

EP    0573586 A1    12/1993
EP    0985394 A2    3/2000
(Continued)

OTHER PUBLICATIONS

International Search Report for PCT/EP2019/080423 issued on Jul. 30, 2020 (with English translation).

*Primary Examiner* — Vishal I Patel
(74) *Attorney, Agent, or Firm* — Collard & Roe, P.C.

(57) ABSTRACT

A method for producing an elastic laminate with at least a first top layer and an elastic film, wherein the first top layer is fed along a production direction to a first stretching device, is subsequently stretched transverse to the production direction by means of the first stretching device and is puckered, and is either connected to an extrusion web provided for forming the elastic film such that the top layer is connected to the extrusion web only by portions facing the melt web or is connected to a pre-produced elastic film in that the elastic film is at least incipiently melted on its side facing the first top layer, the first top layer is pressed against the at least incipiently melted side of the elastic film only by portions, and is therefore at least partially embedded in a polymer matrix of the elastic film.

15 Claims, 7 Drawing Sheets

(51) Int. Cl.
| | |
|---|---|
| *B32B 5/02* | (2006.01) |
| *B32B 5/06* | (2006.01) |
| *B32B 7/05* | (2019.01) |
| *B32B 7/08* | (2019.01) |
| *B32B 27/12* | (2006.01) |
| *B32B 27/32* | (2006.01) |
| *B32B 37/10* | (2006.01) |
| *A61F 13/15* | (2006.01) |

(52) U.S. Cl.
CPC ............... *B32B 7/05* (2019.01); *B32B 7/08* (2013.01); *B32B 27/12* (2013.01); *B32B 27/32* (2013.01); *B32B 37/10* (2013.01); *A61F 13/15642* (2013.01); *B32B 2250/02* (2013.01); *B32B 2255/10* (2013.01); *B32B 2305/20* (2013.01); *B32B 2307/51* (2013.01); *B32B 2307/726* (2013.01); *B32B 2323/00* (2013.01); *B32B 2535/00* (2013.01)

(58) Field of Classification Search
CPC ......... B32B 27/12; B32B 27/32; B32B 37/10; B32B 2250/02; B32B 2255/10; B32B 2305/20; B32B 2307/51; B32B 2307/726; B32B 2323/00; B32B 2535/00; B32B 2555/02; B32B 2274/00; A61F 13/15642

See application file for complete search history.

(56) References Cited

U.S. PATENT DOCUMENTS

| | | |
|---|---|---|
| 10,137,674 B2 | 11/2018 | Kline et al. |
| 10,435,829 B2 | 10/2019 | Hansel et al. |
| 10,654,255 B2 | 5/2020 | Kline et al. |
| 11,021,821 B2 | 6/2021 | Hansel et al. |
| 2005/0101216 A1* | 5/2005 | Middlesworth ......... A61F 13/51 28/155 |
| 2010/0096074 A1 | 4/2010 | Schoenbeck et al. |
| 2011/0160691 A1* | 6/2011 | Ng .................. B32B 27/02 264/145 |
| 2016/0058624 A1 | 3/2016 | Hohm et al. |

FOREIGN PATENT DOCUMENTS

| | | |
|---|---|---|
| EP | 2177654 A1 | 4/2010 |
| EP | 3246444 A1 | 11/2017 |
| WO | 2017184542 A1 | 10/2017 |

* cited by examiner

METHOD FOR PRODUCING AN ELASTIC LAMINATE, AND LAMINATE OBTAINABLE ACCORDING TO SAID METHOD

CROSS REFERENCE TO RELATED APPLICATIONS

This application is the National Stage of PCT/EP2019/080423 filed on Nov. 6, 2019, the disclosures of which are incorporated by reference. The international application under PCT article 21(2) was not published in English.

BACKGROUND OF THE INVENTION

The invention is directed to a method for producing an elastic laminate having at least a first top layer and an elastic film. Further subject matter of the invention is a laminate which is obtainable by means of the method.

The elastic laminate is particularly preferably used as elastic portion of a disposable sanitary article. The elastic laminate is provided particularly as an elastic closure strip of a conventional diaper or also as an elastic side portion of a disposable diaper, also commonly known as training pants. Apart from diapers for babies, corresponding elastic materials are also provided in incontinence articles for older children and adults.

With respect to the cases of use described above, various constraints must be taken into account. On the one hand, the aim in disposable articles is to reduce costs as much as possible and to make the most efficient possible use of materials. Production and processing must also be as simple and economical as possible.

Beyond this, however, the described purposes of use are technically exacting because a high reliability and comfort are necessary. In particular, the described sanitary articles must also have a good fit when the user executes movements so that excretions received therein are safely retained. Further, the described sanitary article should not be unpleasant to the senses or even cause detriment to the user.

For this purpose, known elastic laminates generally have at least one top layer comprising nonwoven which forms a soft, pleasant and fabric-like surface and can be produced inexpensively. In a top layer of this kind which is usually not elastic, the desired elastic recovery properties for a secure fit are achieved by means of the elastic film. As regards the top layer, it must merely be ensured that the formed laminate is sufficiently stretchable.

Different approaches are known from practice for achieving these characteristics of the laminate. For example, a pre-produced elastic film and a pre-produced top layer of nonwoven can be connected to one another in a substantially tension-free manner using pressure and temperature, adhesive or by means of ultrasonic welding, a pattern of connected and unconnected areas preferably being provided. If the nonwoven has only a low strength, the laminate formed in this way can be used directly for the purposes described above.

However, an activation of the formed laminate is often provided during the production process, for which purpose the laminate is stretched in a desired stretching direction, for example, transverse to a production direction. To this end, the laminate can be fed, for example, to a stretching device with ring rolls. Owing to the undulating or zigzag shape of the roll gap of intermeshing ring rolls, the inserted material is lengthened in a transverse direction so that the stretchable but inelastic top layer of nonwoven is overstretched, permanently deformed and possibly also partially destroyed. An elastic recovery occurs when exiting the roll gap because of the elastic films, and the laminate is then easily stretchable subsequently to the degree that it was previously stretched. The elastic properties are then largely determined by the elastic film due to the plastic deformation and/or partial destruction of the top layer.

This approach is described, for example, in EP 0 573 586 B1 and is widely known in practice.

Since the elastic films and the at least one top layer are largely unstretched during the lamination and an activation is also generally provided subsequently, corresponding materials are also referred to as activatable laminate, zero strain laminate or latent elastic laminate.

Although the described laminates have proven themselves, there are specific drawbacks to be taken into account. Since the nonwoven is overstretched and often also partially destroyed during the activation, the laminate can also be further stretched relatively easily to the point of complete destruction during use. A user cannot clearly perceive a stretching limit.

A variant of a zero strain laminate is described in EP 2 177 654 B1, wherein a layer of nonwoven is formed directly on the elastic films at least on one side. In this case, the nonwoven can also be so easily stretchable that there is no need for a previous activation. However, for this very reason there is no stretching limit that can be sensed by a user in this case either.

According to alternative approaches, it is brought about that a top layer of nonwoven which is substantially unimpaired in its structure is only connected to the elastic film at individual portions, particularly line-shaped or point-shaped portions, and is curled up in an undulating manner therebetween. In principle, a structure of this kind can also be achieved when only a portion-by-portion connection is carried out in the laminates described above, for example, by means of adhesive, and the nonwoven material is not destroyed during the activation.

However, this structure is also achieved when the elastic film is stretched along the desired direction of stretching during lamination and is connected to the top layer by portions. After the cessation of tensile forces, the elastic film recovers and accordingly also causes the top layer attached to it to be pushed together in an undulating manner. As an advantageous result, the nonwoven still substantially has its original structure and is only pushed together along the preferred stretching direction. The laminate formed in this way can then be stretched very easily subsequently to the degree of stretching reached during the lamination until the top layer which initially lay on the elastic film in an undulating manner is pulled straight again to a certain extent. Depending on the configuration of the top layer, a very clear stretching limit can be achieved in a particularly advantageous manner. A clearly perceptible steep rise in the force required for further stretching then results in the force-displacement curve of the laminate.

Since the elastic film is stretched during the lamination, a procedure of this kind is also referred to as stretch bonding.

A material with comparable characteristics can be formed when, in accordance with a further variant, the top layer is brought into an undulating shape before being connected to the elastic films along the desired stretching direction and is then connected to the elastic film. A corresponding handling of the top layer can be demanding particularly because the edges of the corresponding material web must be positioned in a sufficiently precise manner. As a result, however, no large tensile forces need be applied to the elastic film during lamination along the desired stretching direction. Since the top layer is pleated or puckered with its undulating shape for the lamination, a corresponding procedure is also known in practice as neck bonding.

A neck bonding of this type is known from EP 0 985 394 B1, although the connection of the top layer to individual elastic strands and not to a film is described therein. However, configurations in which at least one top layer of nonwoven is laminated with an elastic film by means of neck bonding is also known from practice.

The question of whether a material web is stretched or merely puckered by means of intermeshing ring rolls depends upon various factors, such as the shape of the ring rolls and the operative friction. For stretching, it is also often necessary to fix the material webs at the edges thereof as is also provided in the finished laminate according to EP 0 573 586 B1, already cited.

Stretching a top layer before further processing by means of ring rolls is known, for example, from WO 2017/184542 A1. When a structure of the ring rolls remains constant around the circumference, a continuous undulating shape is produced. Alternatively, the structure of the individual protruding rings can also be varied along the circumference so that different structures can also be formed along the production direction. Corresponding steps are known from WO 2017/184542 A1.

Against the background of the prior art, the problem addressed by the present invention is that of providing a method for producing an elastic laminate, wherein the formed laminate is particularly cost effective and has good functional characteristics. Further, a laminate which is obtainable by means of the method is to be provided.

SUMMARY OF THE INVENTION

The subject matter of the invention and the solution to this problem is a method for producing an elastic laminate according to patent claim 1 and a laminate according to patent claim 6 that is obtainable by the method.

Accordingly, the invention is directed to a method for producing an elastic laminate, particularly a transversely elastic laminate, with at least a first top layer and an elastic film, wherein the first top layer as material web is fed along a production direction to a first stretching device, the first top layer is subsequently stretched transverse to the production direction by means of the first stretching device and, in so doing, is puckered, and the puckered first top layer is subsequently so connected in puckered state either to an extrusion web provided for forming the elastic film that the top layer is connected to the extrusion web only by portions on the side of the top layer facing the extrusion web or is connected to a pre-produced elastic film in that the elastic film is at least incipiently melted on its side facing the first top layer, in that the first top layer is pressed against the at least incipiently melted side of the elastic film only by portions, and in that, in so doing, the first top layer is at least partially embedded in a polymer matrix of the elastic film.

According to a first aspect of the invention, it is accordingly provided that the first top layer is also puckered in the course of being stretched by means of the first stretching device, and the folds or wrinkles are then at least partially and preferably at least extensively retained until the lamination. Accordingly, the first top layer is still puckered during the lamination so that a material reserve is provided by the wrinkles for the intended elastic stretching of the formed laminate.

According to a preferred embodiment of the invention, it is provided that the first stretching device is formed by two intermeshing ring rolls, and the first material web can be guided at one of the ring rolls until it is laminated. It can be brought about in this way first that the first material web also initially remains unchanged with respect to its structure with a precisely predetermined width, in particular the starting width of the material web, after the stretching, the material web then being held and guided at the protrusions of the associated ring roll.

In order to hold the first material web with an exact width or at least approximately with a given width, this first material web is advisably held at its edges by the first stretching device and, in particular, is clamped in at annular edges of the ring rolls. When mutually intermeshing rings protruding over a central plane are arranged equidistant between the edges, a stretching which is uniform on the average results between the edges, although a modulation of the stretching corresponding to the spacing of the consecutive rings is possible as a result of the friction and supporting of the first material web at the individual rings, also referred to as teeth. In particular, it can happen as a result that the first material web is stretched less at the points of contact with the rings and stretched more between the rings.

Against this background, however, the invention is not limited to stretching devices in which the rings are arranged equidistant. On the contrary, the spacing of the consecutive rings can also be varied in order to selectively generate areas with different stretchability and, accordingly, to tailor the mechanical characteristics of the laminate more accurately to specific requirements.

Additionally or alternatively, the first material web can be fixed not only at the edges thereof but also at at least one intermediate portion so that it is not stretched at that location but is puckered. A procedure of this kind may be advisable, for example, in order to further process the laminate for multiple uses, i.e., to form at least two consecutive strips in transverse direction. The separation of the at least two consecutive strips is then advisably carried out at the intermediate portion. Because the first material web is then flat and unstretched at the intermediate portion, the strips formed in this way can easily be further processed and, for example, a sanitary article can be glued during production.

In a possibility for adjusting individual rings or ring segments, the gap for connecting to the extrusion web and elastic film, respectively, can then also possibly be optimized.

In a particularly preferable manner, the first material web and the extrusion web and elastic film, respectively, can then be connected in a roll gap between the corresponding ring roll and a mating roll. The top layer can then be pressed against the extrusion web or elastic film effectively and with a comparatively large force at the individual protrusions, which results in a particularly intimate and reliable connection, while the top layer remains at a distance from the extrusion web of the elastic film between the protrusions and, accordingly, no connection is carried out there.

According to a preferred embodiment, the extrusion web provided for forming the elastic film is first formed inline immediately before the lamination in the method for producing the elastic laminate. In particular, it can be provided within the scope of the invention that the single-layer or multiple-layer extrusion web is still molten from the immediately preceding extrusion process, or is at least not completely solidified, at least on the side thereof facing the first top layer. Even if the corresponding surface is initially solidified after the extrusion process, the surface can then be reheated for laminating and at least incipiently melted so that it is then possible to laminate without additional adhesive and, therefore, without introducing further chemical components. In case of a multiple-layer configuration of the extrusion web, different melting points can also be provided for the different layers. Accordingly, it can be particularly expedient for the procedure when, for example, a layer remote of the first top layer or a core layer of the extrusion web is already completely or extensively solidified during the lamination and a certain solidity is already imparted to the extrusion web.

According to an alternative configuration, a pre-manufactured elastic film is supplied and is then at least incipiently melted at the side thereof facing the top layer before connecting to the top layer. The actual connection is then carried out, as previously described in connection with the extrusion web, only by pressing together the layers to be connected without additional adhesive and, therefore, without introducing further chemical components. In view of the corresponding connection process, the steps described in the following in connection with the extrusion web are usually also suitable for the procedure in which a pre-manufactured elastic film is supplied.

The pressing forces which are greater when acting on the individual protrusions than when acting over the whole surface area are especially advantageous for achieving a high local interlayer adhesion. While the unconnected areas forming wrinkles remain soft and movable, a particularly intimate connection is produced by the higher pressing forces. In particular, local pressing forces can be achieved which are difficult to apply or could damage the material in the case of a planar connection. Within the framework of the invention, however, a certain compression of the first top layer solely at the connected portions is acceptable. With regard to pressing forces, there is a larger permissible range of parameters, which can also be referred to as process window, compared to pressing over the entire surface area. There is also a larger possible selection of materials for the first top layer. However, different aspects can play a part with respect to details. Thus it is possible that the first top layer is pressed into the extrusion web or the elastic film or at least an associated layer of the extrusion web or elastic film to a certain extent.

If, for example, according to a preferred configuration of the invention, a nonwoven is supplied as first material web, the individual fibers of the nonwoven can be enclosed by the polymer of the extrusion web or of the at least incipiently melted elastic film so that a separation is possible only by destroying or at least partially destroying the first top layer in case of a maximum interlayer adhesion.

Alternatively, the first material web can also be formed, for example, by a film, a woven or a knit. It need only be ensured that the first material web can be stretched transverse to the production direction and puckered in the process.

When the first material web has openings, perforations or free spaces, a connection can be achieved by a kind of positive engagement, as was described above in connection with a nonwoven, when the polymer of the extrusion web or the at least incipiently melted elastic film penetrates into the openings, perforations or free spaces.

Additionally or alternatively, it can be provided in all of the possible configurations of the first material web that component parts of the first material web are melted or incipiently melted when laminating with the extrusion web and elastic film, respectively, by pressure and temperature. When the first material web is formed, for example, by a film, it can have a low melting point cover layer. When the first material web is formed of fibers or threads, the latter can also have component parts with low melting points and component parts with high melting points, for example, as a fiber-thread mixture, by means of different filaments or a bicomponent construction.

Additionally or also alternatively, it can also be provided that the first top layer is melted or at least incipiently melted at least partially owing to the temperature of the extrusion web or of the at least incipiently melted elastic film so that the materials can be reliably welded to one another. If, as was already described, a nonwoven is used as first material web, the fibers forming the nonwoven can also be optimized in this respect.

For example, a nonwoven can be formed from different fibers with a different melting point or softening temperature. The method can then be carried out in such a way that only a portion of the fibers is melted or incipiently melted and enables a particularly reliable connection, while another portion of the fibers is not melted or incipiently melted and accordingly ensures the structural integrity of the nonwoven.

Additionally or alternatively, at least a portion of the fibers can also take the form of multi-component fibers and particularly bicomponent fibers. In the case of bicomponent fibers, for example, a high melting point core can be combined with a low melting point sheath. It is then advisably provided that only the low melting point sheath is melted or incipiently melted.

The mating roll described above is also referred to as a smoothing roll because the extrusion web is guided and supported thereon. The mating roll can advisably be tempered in order to achieve desired characteristics during the lamination and further transport of the formed laminate. Accordingly, it is advisable that at least an excessive flowing of the corresponding polymer is prevented after the extrusion web is connected to the first top layer. The smoothing roll or mating roll is therefore also frequently referred to in practice as a chill roll.

It is preferably provided that a top layer is arranged in each instance on both sides of the extrusion web or elastic film, respectively. Different variants are contemplated for this purpose. For example, a second top layer is arranged opposite the first top layer described above and, as was described above, the second top layer is also advisably fed along a production direction to a second stretching device, stretched transverse to the production direction by means of the second stretching device and puckered in the process, and the second top layer is subsequently connected to the extrusion web so as to be puckered.

In this respect, it must be taken into account that the extrusion web preferably exiting from a casting die is cooled after leaving the extrusion gap so that the two top layers must then be supplied and laminated in a timely manner before the polymer melt is cooled too much.

It is conceivable in principle that an exactly or substantially symmetrical procedure is carried out for a configuration with two top layers, and the lamination of the two top layers is then carried out in a roll gap formed by two opposing ring rolls. However, for a procedure of this kind the teeth of the ring rolls must be exactly opposite one another, and the extrusion web is not guided between the teeth. To enable the simultaneously symmetrical or substantially symmetrical feed and lamination of two top layers, various specific adaptations may be advisable. For example, it is advisable when the extrusion web, while still soft enough for an intimate connection to the top layers, already has a certain melt strength. Otherwise, the molten web between the opposing teeth could be thinned out excessively. A multilayer configuration with at least three layers which will be further described later may also be advisable, in which case, for example, during lamination, a core layer also substantially retains its previous thickness at the connection points because of the cooling that has already taken place and/or because of its viscosity. When the ring rolls are opposite one another, the rings can also be planar or at least flattened at their outer circumference in order to achieve a reliable connection in spite of any slight misalignment.

When, in accordance with the above-described variants of the invention, a pre-manufactured elastic film is supplied instead of the extrusion web, also, for example, when both sides are heated for an incipient melting of the surfaces, the energy input can also be provided in such a way that at least one core, or a core layer of the elastic film, is not melted and can accordingly also withstand the portion-by-portion compressive forces.

According to a preferred further development of the invention, it is provided that the first top layer and the second top layer are supplied successively with an offset relative to one another and are connected to the extrusion web or the elastic film. It is self-evident that the distance between the two locations for laminating with the two top layers is then kept as short as possible.

In order to allow a connection by means of thermobonding on both sides of the extrusion web and elastic film, respectively, with a certain offset, a polymer material can also be provided for the extrusion web or the elastic film, which polymer material can be processed over a greater temperature range so that at least somewhat different temperatures can be tolerated during lamination of the first top layer on the one hand and the second top layer on the other hand.

It must also be taken into account in this respect that the extrusion web and elastic film, respectively, can be constructed to have multiple layers, in which case a different thermal behavior is also advisable with respect to the different layers. For example, when a core layer and, on both sides respectively, a low melting point cover layer is provided for forming the elastic film, a sufficient stability of the polymer melt of the resulting elastic film and of the laminate can be achieved through the solidification of the core layer after extrusion, while the low melting point cover layers then initially allow a connection to the top layers which are preferably formed of nonwoven. Corresponding cover layers can possibly also be incipiently melted again more easily.

When two top layers are laminated in consecutive steps with the extrusion web of the elastic film according to the preferred configuration of the invention described above, the corresponding side of the extrusion web or elastic film can then possibly also be reheated to a desired temperature before the lamination of the second top layer, hot air or infrared radiation, for example, being contemplated for this purpose.

As was already described in the introductory part, the first top layer and possibly the second top layer are stretched in the same manner with the associated stretching device and, in so doing, simultaneously puckered. In this respect, it is possible that the top layer or top layers extend over the same width before and after stretching even if the top layer or top layers have a greater width per se due to the undulating shape after stretching.

Accordingly, the first top layer and possibly also the second top layer can be fed to the respective associated stretching device with a width which approximately corresponds to, preferably exactly corresponds to, the width of the extrusion web and elastic film, respectively, during the lamination.

It is also advisable when the first material web and possibly the second material web is held by the edges thereof in the associated stretching device so that the width covered by the material web transverse to the production direction is kept constant. The lengthening of the top layer itself which is required for providing a stretchability of the laminate is then carried out in that the corresponding top layer is stretched and puckered in an undulating manner.

According to a further variant, an elastic laminate with two top layers opposite one another can also be formed in that two portions of the above-described elastic laminate with the elastic film and with only the first top layer on the elastic film are connected to one another. A configuration of this kind is also referred to within the framework of the invention as a double laminate so that it may be more easily distinguished.

The double laminate can be formed in that two webs of the laminate with the elastic film and with only the first top layer are fed, and the sides having the elastic film, respectively, face one another. A connection of the elastic films is then carried out at that location. The two fed laminates can be constructed differently or identically in principle. For example, different cover layers can be provided depending on the intended application. The elastic films of the two laminates which are fed as a web are preferably formed from the same material so that they can easily be connected to one another and, further, in the case of a double laminate, form a substantially consistent elastic core. It is possible to carry out a connection in different ways depending on the utilized material. If the elastic film is also comparatively soft and sticky owing to its elastic properties, a sufficient connection may be sufficient in some cases solely by means of pressure, for example, compression in a roll gap. The elastic films facing one another can preferably be heated at least superficially for a lamination in order to achieve a sturdy and reliable connection using simple means. A corresponding heating is possible, for example, with infrared radiation and/or hot air.

Further, the double laminate described above can also be formed in that a web of the laminate comprising the elastic film and only the first cover layer on the side of the elastic film is folded on itself along a folding edge extending in production direction. When this takes place immediately after the connection of the extrusion web of the first cover layer, the elastic film or the extrusion web is in some cases still sufficiently hot and sticky enough that a connection of the double-layer elastic film to itself in the folded state is possible without further heating. Of course, heating can also be provided by means of infrared radiation and/or hot air within the framework of the described embodiment form.

It should be noted in this regard that the formation of the double laminate from two portions of the laminate can be carried out entirely separate (offline) from the formation of the laminate itself. The laminate can be formed in a separate, closed process and possibly transferred. A web of the laminate can then be folded for forming the double laminate or cut into two half-width sheets. Further, two sheets of the laminate produced beforehand can also be provided for forming the double laminate so that no folding or cutting is needed.

According to the invention, the laminate has at least one first top layer. Variants with two top layers which are puckered and connected to the extrusion web of the elastic film have also already been described on this basis. In principle, however, other variants in which the first top layer is puckered as described, but a second top layer has a different configuration are also possible. For example, a material which is only weakly bonded and is easily stretchable, particularly a nonwoven, can also be provided as second top layer. Such easily stretchable material need not be puckered in order to enable a sufficient stretchability of the laminate in its entirety. The mechanical characteristics of laminates, such as the force required for stretching, the elastic recovery forces and a noticeable stretching limit, are then substantially provided or determined by the elastic film and the puckered first top layer. During the production of the described variant, it can preferably be provided that the second top layer is initially connected in a planar manner to the extrusion web, while the latter is still largely molten and therefore very sticky after exiting from a die gap. A reliable connection can then be achieved even when there is a comparatively slight laminar or portion-by-portion contact pressure. The puckered first top layer is connected to the extrusion web subsequently, and pressing forces which are relatively large locally can easily be provided by connecting merely along line-shaped portions.

The first material web and possibly also the second material web can be stretched by the associated stretching device, for example, by a value between 100% and 400%, particularly between 150% and 350%, with respect to an initial length. If the material web or material webs are then laminated with a corresponding undulating shape, this value also corresponds approximately to the stretchability of the laminate until the initially undulating top layer lying on the elastic film is substantially pulled straight again, and a stretching limit is then usually clearly noticeable to a user.

The present invention also has a further advantage in this respect. On the one hand, as a result of the stretching of at least the first top layer which is provided according to the invention, the material, i.e., particularly the nonwoven, can be made thinner so that (with respect to the stretched state of the laminate) the basis weight of the top layer is reduced. On the other hand, the stretching is also carried out in the stretching device in such a way that the associated top layer which is preferably formed by a nonwoven is not destroyed with respect to its structure.

The particular effect of the stretching of the top layer or top layers depends not only on the degree of stretching but also substantially on the material of the top layer, and different types of nonwoven can also have different characteristics.

Thus nonwoven materials are available in which a relatively slight stretchability is observed initially in a force-displacement curve, the fiber structure being spread apart in the manner of a net. The material is then made thinner but its actual structure is not destroyed. A relatively abruptly occurring rise in force with increasing stretching is then sometimes observed in the force-displacement curve. This area of the curve may also be referred to as a knee. Appreciably higher forces are then necessary for further stretching but can also lead to destruction of the material. Before the nonwoven finally tears, the force necessary for further stretching usually decreases again appreciably.

The characteristic curve described above in which a knee is formed can also be characterized in that the force-displacement curve has an inflection point. Accordingly, it is provided according to a preferred configuration of the invention that a nonwoven is used which has a force-displacement curve in which an inflection point occurs in a range between 100% elongation and 300% elongation. The elongation at tear of the nonwoven usually amounts to at least 300%, preferably at least 400% and in particular at least 500%.

Taking into account the characteristic curve described above, the initially slight stretching can readily be provided in order to thin out the material and therefore produce a particularly soft and low-cost laminate. When, within the framework of the invention, the stretching is then carried out approximately until the inflection point or knee described above, the subsequent steep rise in force in the force-displacement curve is retained with additional stretching and acts as a distinctly noticeable stretching limit in the laminate formed in this way.

The described characteristic curve exists particularly in reinforced nonwoven materials, the nonwoven having at least one spunlace layer according to a first preferred configuration of the invention. A spunlace nonwoven is a nonwoven which is reinforced or needle-punched by water jets.

Additionally or alternatively, the nonwoven can also have at least one spunbond layer. In this connection, a configuration in which the corresponding spunbond layer has crimped fibers or is made up entirely of crimped fibers is particularly preferred. The crimping can be attributed, for example, to a mechanical crimping and/or the use of bicomponent fibers with an eccentric fiber material structure. For example, when polymer materials with different shrinkage behaviors are arranged side by side in bicomponent fibers, a crimping can result already during cooling or by means of an additional thermal treatment.

The crimping of the fibers can be advantageous for various reasons within the framework of the invention. Accordingly, corresponding spunbond layers are pleasantly soft for a user because of the crimping of the fibers. For this reason, nonwoven materials of this kind are also referred to in practice as high-loft nonwovens. The high degree of softness comes to the fore particularly when the spunbond layer with crimped fibers forms a surface of the laminate. Corresponding nonwovens and advantages thereof are described, for example, in EP 3 246 444 A1.

Spunbond layers of crimped fibers are also characterized by excellent stretchability. During stretching, the crimped fibers can easily be pulled straight initially to a certain extent along the stretching direction without destroying the structure of the corresponding nonwoven layer. If, as was described, only a portion of the fibers is crimped in a nonwoven or a layer of the nonwoven, at least this portion can be stretched to a certain degree without being destroyed.

In principle, however, other nonwoven materials can be contemplated. In particular, a multilayer nonwoven can also be used. The mechanical and haptic properties of the nonwoven can be precisely adjusted and selected particularly in such a multilayer construction.

In principle, it is also possible that the entire nonwoven, a layer of the nonwoven or at least a portion of the fibers of a layer is formed from nonmelting fibers, such as viscose, cotton or cellulose, for example. Nonmelting fibers can be provided, for example, to impart specific properties, such as a certain absorbency, to the proportion of renewable raw materials or to the laminate.

If a thermobonding is carried out within the framework of the invention by means of pressure and temperature, additional adhesive can be dispensed with. In addition to a corresponding cost savings, other drawbacks sometimes entailed by adhesives are prevented, for example, the release of volatile components.

As has already been described, the extrusion web or the elastic film can be formed of multiple layers. For example, in a three-layer construction, a core layer of thermoplastic elastomer can be combined with non-elastic cover layers.

In a single-layer or multilayer configuration of the extrusion web or elastic film, conventional styrenic block copolymers and thermoplastic polyolefin elastomers (TPE-o), which are often formed by a polypropylene copolymer, are contemplated as thermoplastic elastomers. At least one elastic layer is to be provided in case of a multilayer construction. For example, a core layer of elastic polyolefin can be arranged between thin cover layers which are likewise formed from polyolefin. Particularly when the cover layers are comparatively thin, it is not necessary for the cover layers to be formed from an elastic polyolefin.

The subject matter of the invention is also a laminate which is obtainable by means of the method described above.

The laminate has a first top layer of nonwoven and an elastic film, the first top layer and the elastic film being connected only at continuous or uninterrupted portions extending along a longitudinal direction by means of thermobonding with the film. The first top layer is arranged on the film along a transverse direction in an undulating manner with bows between the connected portions. The first top layer has at least twice the width of the film along the transverse direction, including the undulation with the exposed bows, and the film is unstretched after its forming of the laminate by means of thermobonding and preferably also proceeding from the production of the film itself. The bows are usually exposed between the connected portions. Especially with a comparatively minimal stretching and, therefore, a less pronounced undulation, it is not ruled out that at least individual fibers of a nonwoven, as preferred top layer, are easily connected to the film at the bows.

It is preferably provided that the top layer has a basis weight between 10 g/m$^2$ and 80 g/m$^2$ in the unstretched state with respect to the area of the laminate. When the top layer is held at its edges during stretching, as was described already in connection with the method, and the surface covered in transverse direction remains unchanged, the specified basis weight also corresponds to the basis weight initially provided in the corresponding material web. An appreciably lower basis weight results with respect to the stretched state of the laminate or taking into account the actual length of the top layer. Also as a direct result of this, a particularly efficient use of materials is achieved within the framework of the invention.

As is also apparent from the method, the first top layer is given an undulating form by means of stretching. Further possible configurations of the laminate itself will also be apparent from the description of the method.

BRIEF DESCRIPTION OF THE DRAWING FIGURES

The invention will be described in more detail in the following referring to drawings in which only one embodiment example is depicted. The drawings show.

DETAILED DESCRIPTION OF THE INVENTION

Figure 1:
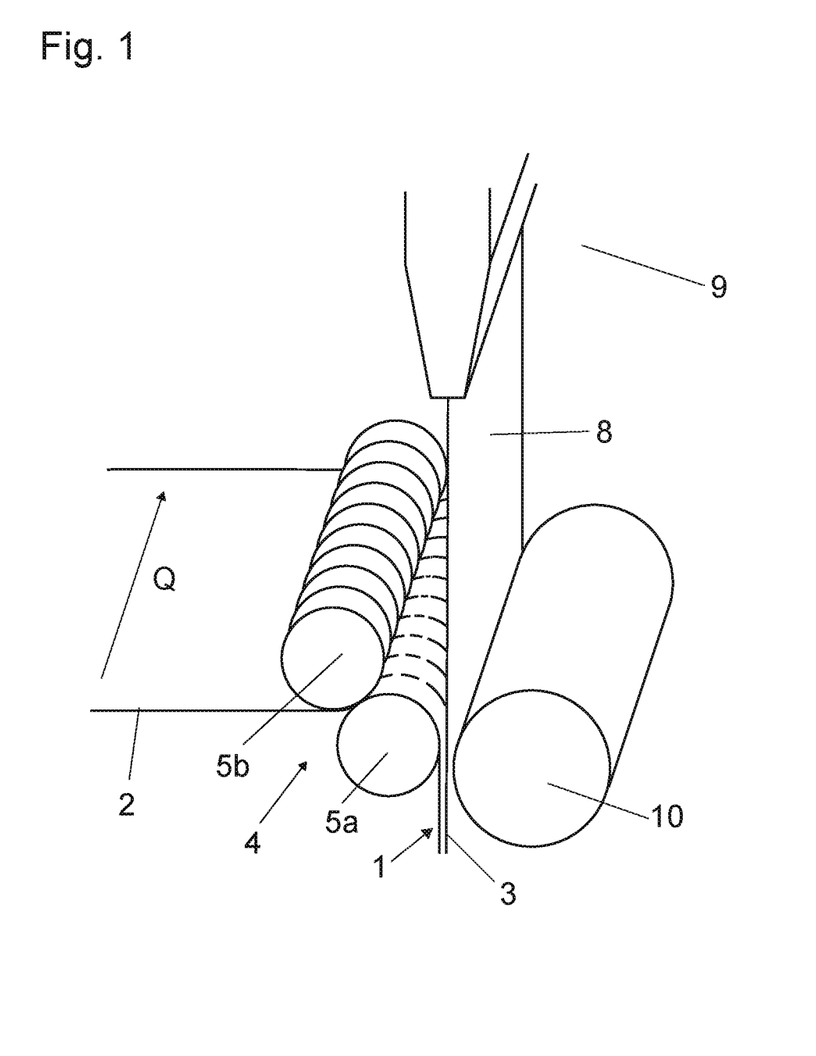
FIG. 1 essential steps of a method for producing an elastic laminate.

FIG. 1 shows a method for producing an elastic laminate 1 with a first top layer 2 and an elastic film 3. A spunlace nonwoven is provided as first top layer 2. The first top layer 2 is fed to a stretching device 4 along a production direction. Within the meaning of the invention, production direction refers to the forward feed direction of the material web of the first top layer 2, although, of course, the production direction changes correspondingly in case of a deflection at rolls. The assignment of the production direction serves to delimit and define a transverse direction Q. Thus when a plurality of portions or material webs are fed as a continuous web, there is no need to distinguish between the different feed devices.

Figure 2:
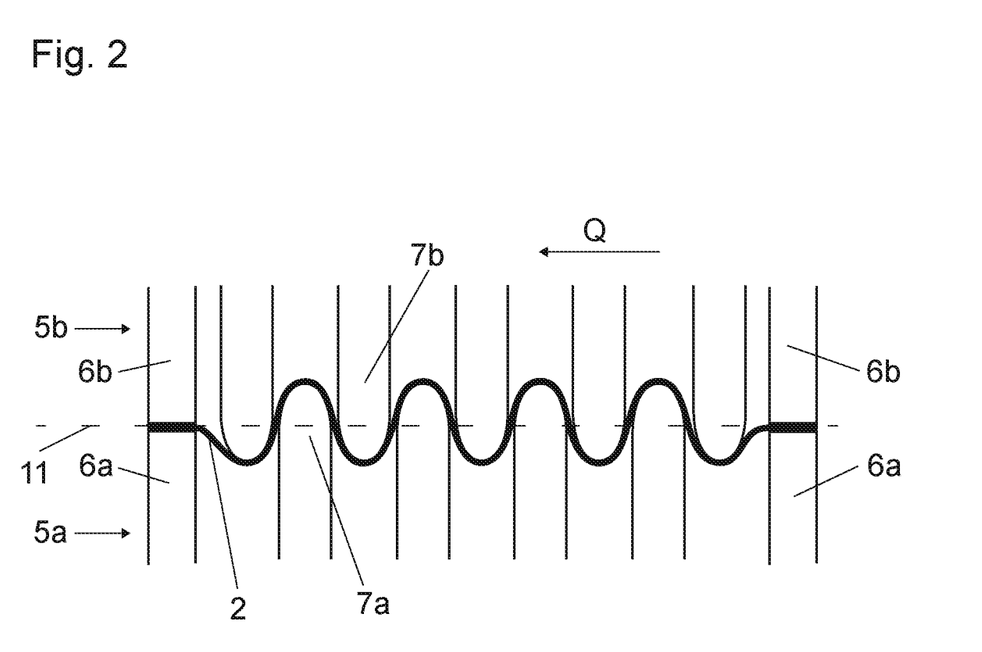
FIG. 2 the method step of stretching a top layer.

The first stretching device 4 has two intermeshing ring rolls 5a, 5b which are shown with the top layer 2 arranged therebetween in cross section in FIG. 2. When FIGS. 1 and 2 are viewed in combination, it will be appreciated that the material web of the first top layer 2 is held at edges 6a, 6b of the ring rolls 5a, 5b, the ring rolls 5a, 5b being provided, respectively, between the edges 6a, 6b with rings 7a, 7b protruding relative to a central plane M in the form of teeth. Because the material web of the first top layer 2 is held at the edges 6a, 6b, the width covered by the first top layer 2 in transverse direction Q also does not change in the first stretching device 4. However, the intermeshing rings 7a, 7b cause a lengthening, i.e., stretching, of the material web of the first top layer 2. The degree of stretching results from the shape of the rings 7a, 7b and from the offset relative to the central plane M.

The elongation usually amounts to between 50% and 400%, in particular between 100% and 350%, preferably between 150% and 300%.

The first top layer 2 is guided at the first stretching device 4 such that the first top layer 2 continues to contact and be guided by one of the ring rolls 5a also after exiting the roll gap. The first top layer accordingly substantially retains the structure shown in FIG. 2 after leaving the roll gap.

While the first top layer is then guided at the associated ring roll 5a, a lamination of the first top layer 2 with an extrusion web 8 exiting from a casting die 9 is carried out. The lamination of the first top layer 2 with the extrusion web 8 is carried out between a roll gap of the associated ring roll 5a and a mating roll 10 which cools the extrusion web 8 and accordingly also smooths and fixes it. The mating roll 10 can therefore also be referred to as smoothing roll or chill roll.

Because the first top layer 2 is guided at one of the ring rolls 5a when laminated with the extrusion web 8, the first top layer 2 and the extrusion web 8 are only connected at line-shaped portions 11, while the first top layer 2 also substantially retains the undulating shape with wrinkles, shown in FIG. 2, between portions 11. Exposed bows 12 which contribute to a particularly soft and pleasant tactile impression remain between the connected portions 11 (see FIG. 3a).

Figure 3A:
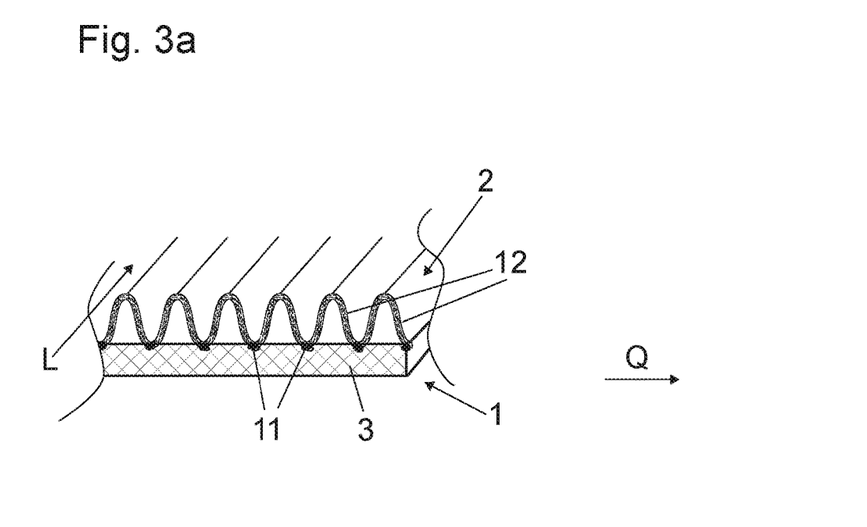
FIG. 3a a schematic view of an elastic laminate in cross section.

According to FIG. 3a, the portions 11 are continuous in production direction and, therefore, in a longitudinal direction L of the laminate 1. In principle, however, it is also possible that the portions 11 are interrupted along the longitudinal direction L. This can be achieved in that the individual rings 7a, 7b are interrupted, i.e., segmented, along the circumferential direction of the associated ring rolls 5a, 5b.

Figure 3B:
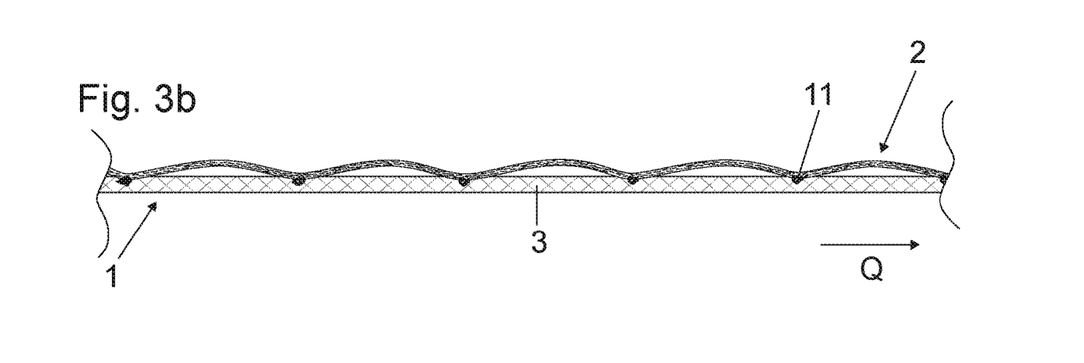
FIG. 3b the laminate according to FIG. 3a in the stretched state.

According to FIG. 3b, the laminate 1 is stretched to the extent that the bows 12 shown in FIG. 3a are spread apart such that the first top layer 2 then lies substantially flat on the elastic film 3. The width of the laminate along the transverse direction Q then corresponds to the total width of the first top layer taking into account the undulating shape. Accordingly, as a result of the degree of stretching shown in FIG. 2 in the first stretching device 4, a stretching limit is also determined for the entire laminate 1. The laminate is stretchable relatively easily until the configuration shown in FIG. 3b is reached, the elastic film 3 being substantially decisive for the elastic properties and the forces required for stretching.

When the configuration shown in FIG. 3b is reached, the first top layer 2 is pulled taut and causes a distinctly noticeable stretching limit which is perceived by a user as a kind of stop. As a result of these steps, the laminate 1 can be unintentionally overstretched during use and therefore destroyed in certain cases.

Figure 4:
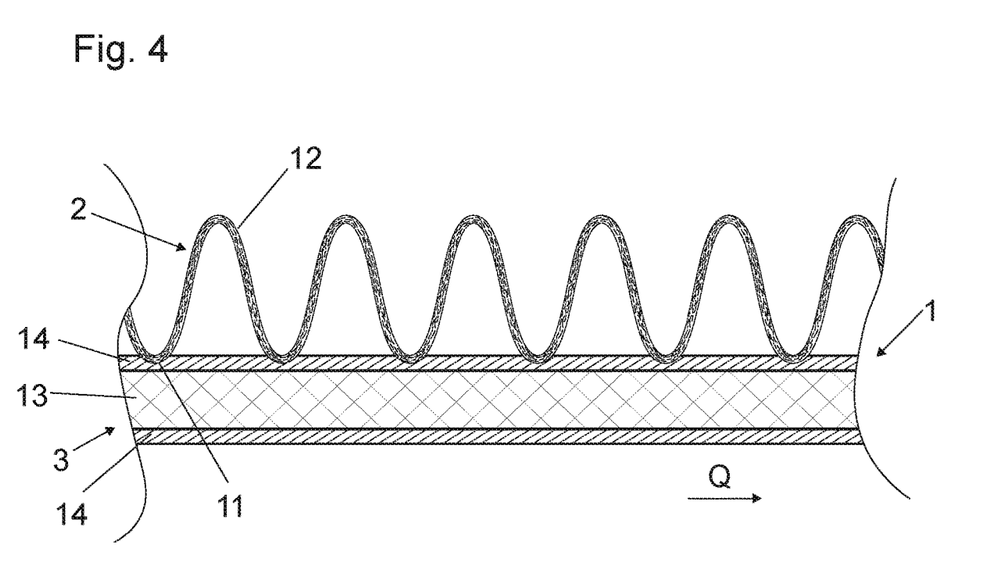
FIG. 4 a cross section according to FIG. 3a for an alternative configuration of the elastic laminate.

Without limiting generality, the extrusion web 8 and the elastic foil 3 formed from it can have one or more layers. In this connection, FIG. 4 shows an exemplary three-layered construction of the elastic film 3, a core layer 13 of thermoplastic elastomer being arranged between cover layers 14 which are preferably not elastic or minimally elastic. Especially in the case of thin cover layers 14 at any rate, an elasticity is not necessary for the basic function of the laminate. In this respect, it can also be provided that the cover layers 14 comprise a low melting point material so that the core layer 13 forms a closed homogeneous layer relatively quickly after exiting from the casting die 9, while the cover layers 14 are still available for an excellent lamination of the at least first top layer 2. It can also be provided that the first top layer 2 which is preferably formed from nonwoven penetrates into the extrusion web 8 and particularly the cover layers 14 by means of the lamination. At the connected portions 11, the nonwoven is accordingly embedded in the elastic film 3 particularly reliably and can then be separated again only by destroying it.

Additionally or alternatively, it can also be provided that the top layers formed from nonwoven have differently melting fibers and/or bicomponent fibers. With bicomponent fibers, a low melting point sheath, for example, can be provided around a high melting point core so as likewise to contribute to a particularly high bond strength as result of the sheath melting when connecting to the extrusion web 8. A similar effect can be achieved in a fiber mixture by means of a proportion of low melting point fibers. Within the framework of the invention, nonmelting fibers, such as viscose or cotton, for example, can also be provided, these nonmelting fibers being pressed into the extrusion web during production and accordingly mechanically connected.

Figure 5:
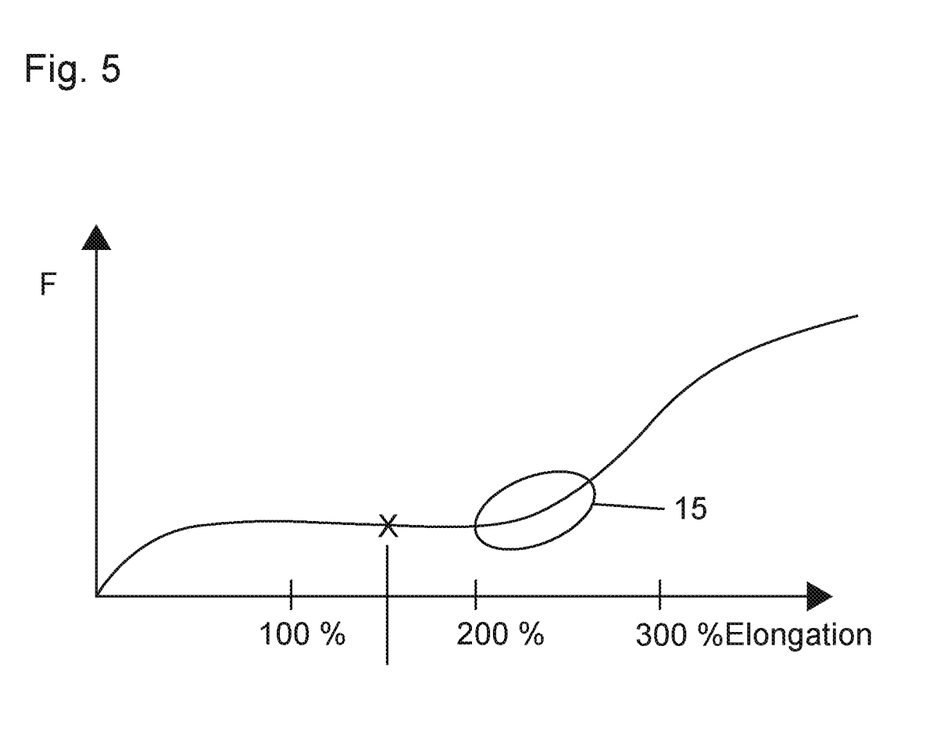
FIG. 5 a force-displacement curve for a top layer of the laminate.

As has already been mentioned, a spunlace nonwoven, for example, is particularly suitable as top layer 2. To this end, according to FIG. 5, a typical force-displacement curve is shown by way of example, wherein the nonwoven has an inflection point WP in a range between 100% elongation and 300% elongation. Subsequent to the inflection point WP, the force F necessary for further stretching rises sharply so that the force-displacement curve has a kind of knee 15. The nonwoven is advisably stretched approximately to the inflection point WP or knee 15 before lamination, as is shown in FIG. 2, so that the material is thinned in an advantageous manner without losing its structure. However, the appreciable rise in force following the knee 15 is then also retained in respect of the laminate 1 so that the distinctly noticeable stretching limit described above is ensured. The elongation at tear of the nonwoven is typically above 100%, preferably above 150% and particularly above 200%. Depending on the configuration of the nonwoven, however, the elongation at tear can also lie above 300%, 400% or even 500%.

Figure 6:
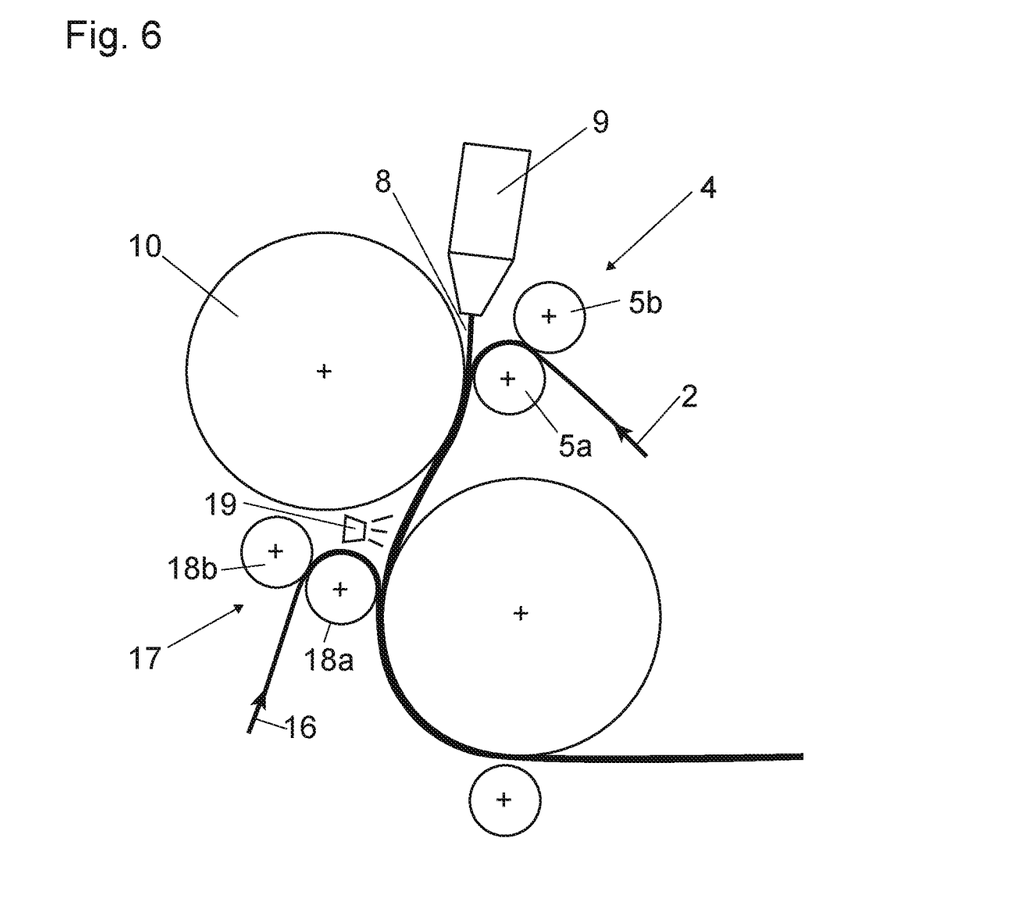
FIG. 6 a further development of the method according to FIG. 1.

According to a further development of the invention, it is provided that the laminate also has a second top layer 16 opposite the first top layer 2. This second top layer 16 can be formed in the manner described above in connection with the first top layer 2. Accordingly, the second top layer 16 is correspondingly fed to a second stretching device 17 with ring rolls 18a, 18b. The statements respecting the first stretching device 4 are referred to for further details in this regard.

The second top layer 16 is laminated with the extrusion web 8 with a slight offset. In this respect, it must be ensured that during the lamination with the second top layer 16 the extrusion web 8 is not yet solidified to the extent that a connection is no longer possible. To this end, referring to FIG. 4, it may also be advantageous when a core layer 13 of thermoplastic elastomer is combined with cover layers 14 which have a lower melting point and accordingly remain fluid or at least soft even when there is a drop in temperature.

In principle, it is also possible to reheat the corresponding surface of the extrusion web 8 to a certain extent prior to the lamination of the extrusion web 8 with the second top layer 16. An exemplary heating device 19 is shown in FIG. 6. The heating device 19 can provide heating by means of hot air and/or infrared radiation, for example.

Figure 7:
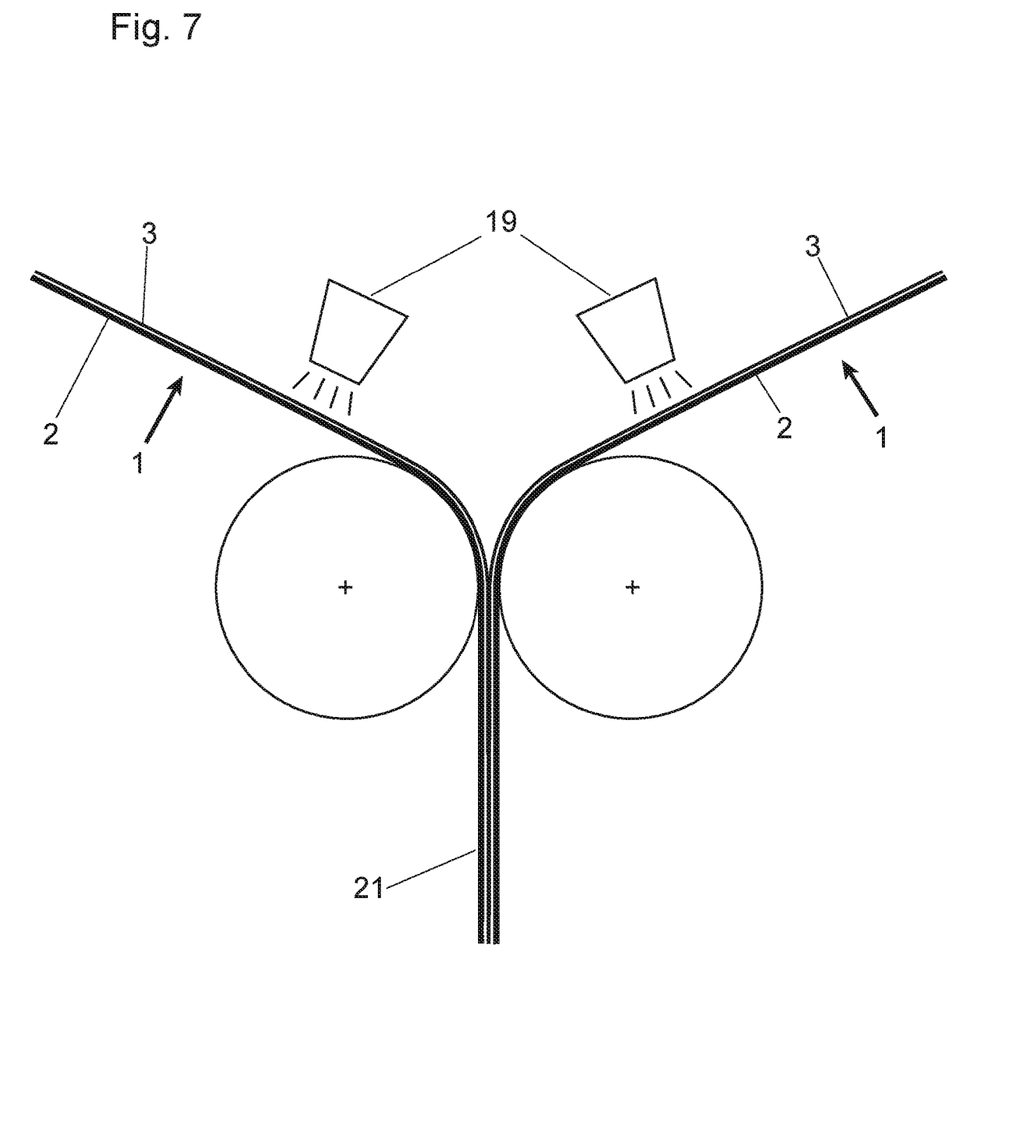
FIG. 7 the formation of a double laminate.

The embodiment form shown in FIG. 6 makes it possible to arrange the first top layer 2 and the second top layer 16 on both sides of the extrusion web 8. With this in mind, FIG. 7 shows an alternative configuration in which two laminates 1 formed beforehand, each with only the elastic film 3 and the first top layer 2, are fed such that the elastic films 3 face one another. After an at least superficial heating by means of heating devices 19, a connection is carried out in a roll gap. The two elastic films 3 lying one on top of the other accordingly interlock to form an extensively consistent elastic core 20. Therefore, a kind of double laminate 21 is formed from two portions of the laminate 1.

What is claimed is:

1. A method for producing an elastic laminate (1) with at least a first top layer (2) and an elastic film (3), wherein
   a) the first top layer (2) as first material web is fed along a production direction to a first stretching device (4),
   b) the first top layer (2) is subsequently stretched transverse to the production direction by means of the first stretching device (4) and, in so doing, is puckered, and either
   c) the puckered first top layer (2) is subsequently connected to an extrusion web (8) provided for forming the elastic film (3) such that the top layer (2) is connected to the extrusion web (8) only by portions (11) on the side of the top layer (2) facing the extrusion web (8), or
   d) the puckered first top layer (2) is subsequently connected to a pre-produced elastic film (3) in that the elastic film (3) is at least incipiently melted on a side facing the first top layer (2), in that the first top layer (2) is pressed against the at least incipiently melted side of the elastic film (3) only by portions (11), and in that, in so doing, the first top layer (2) is at least partially embedded in a polymer matrix of the elastic film (3).

2. The method according to claim 1, wherein the first stretching device (4) is formed by two intermeshing ring rolls (5a, 5b).

3. The method according to claim 2, wherein the first material web and the extrusion web (8) or the elastic film (3) are connected in a roll gap between one of the ring rolls (5a) and a mating roll (10).

4. The method according to claim 1, wherein a second top layer (16), as second material web, is fed to a second stretching device (17), stretched transverse to the production direction by means of the second stretching device (17) and puckered by the stretching, and wherein the second top layer (16) is subsequently connected to the extrusion web (8) or elastic film (3) so as to be puckered.

5. The method according to claim 1, wherein the first material web is stretched by means of the first stretching device (4) by a value between 100% and 400%.

6. The method according to claim 1, wherein a nonwoven is fed as the first material web.

7. The method according to claim 6, wherein the nonwoven has at least one spunlace layer.

8. The method according to claim 6, wherein in the nonwoven has at least one spunbond layer.

9. The method according to claim 8, wherein the spunbond layer contains crimped fibers and is formed from crimped fibers.

10. The method according to claim 6, wherein the nonwoven has an elongation at tear of at least 300%, and wherein a force-displacement curve of the nonwoven has an inflection point (WP) in a range between 100% elongation and 300% elongation.

11. The method according to claim 6, wherein the nonwoven contains bicomponent fibers.

12. The method according to claim 1, wherein the extrusion web (8) or the elastic film (3) is formed of multiple layers with a layer of thermoplastic elastomer and at least one cover layer (14).

13. The method according to claim 1, wherein the extrusion web (8) or the elastic film (3) is formed of polyolefin.

14. The method according to claim 1, wherein the first top layer (2) is fed to the first stretching device (4) with a width which corresponds to between 90% and 110% of the width of the extrusion web (8) or the elastic film (3) during the lamination.

15. The method according to claim 1, wherein the first material web is held at edges thereof in the first stretching device (4).

\* \* \* \* \*